(12) United States Patent
Samadpour

(10) Patent No.: US 8,389,233 B2
(45) Date of Patent: *Mar. 5, 2013

(54) MODULAR COMPOSITING-MULTIPLE LOT SCREENING PROTOCOLS FOR DETECTION OF PATHOGENS, MICROBIAL CONTAMINANTS AND/OR CONSTITUENTS

(75) Inventor: Mansour Samadpour, Seattle, WA (US)

(73) Assignee: Institute for Environmental Health, Inc., Lake Forest Park, WA (US)

(*) Notice: Subject to any disclaimer, the term of this patent is extended or adjusted under 35 U.S.C. 154(b) by 694 days.

This patent is subject to a terminal disclaimer.

(21) Appl. No.: 12/360,796

(22) Filed: Jan. 27, 2009

(65) Prior Publication Data

US 2009/0258359 A1   Oct. 15, 2009

Related U.S. Application Data

(63) Continuation of application No. 11/199,871, filed on Aug. 8, 2005, now Pat. No. 7,534,584.

(60) Provisional application No. 60/599,473, filed on Aug. 6, 2004.

(51) Int. Cl.
| | |
|---|---|
| C12Q 1/08 | (2006.01) |
| C12Q 1/04 | (2006.01) |
| C12Q 1/06 | (2006.01) |
| C12Q 1/10 | (2006.01) |
| C12Q 1/20 | (2006.01) |
| G01N 33/53 | (2006.01) |
| G01N 33/573 | (2006.01) |
| C12Q 1/14 | (2006.01) |
| C12Q 1/18 | (2006.01) |
| C12Q 1/22 | (2006.01) |
| C12M 1/00 | (2006.01) |

(52) U.S. Cl. ............ 435/34; 435/7.2; 435/7.32; 435/31; 435/32; 435/33; 435/36; 435/38; 435/39; 435/40; 435/308.1; 435/849; 435/973

(58) Field of Classification Search .................. 435/7.2, 435/7.32, 31, 32, 33, 34, 36, 38, 39, 40, 308.1, 435/849, 973

See application file for complete search history.

(56) References Cited

U.S. PATENT DOCUMENTS

| | | | |
|---|---|---|---|
| 6,080,437 | A | 6/2000 | Mauer et al. |
| 7,534,584 | B2 * | 5/2009 | Samadpour ..................... 435/34 |
| 7,919,232 | B2 | 4/2011 | Samadpour |
| 2004/0241773 | A1 | 12/2004 | Samadpour |
| 2009/0258359 | A1 | 10/2009 | Samadpour |

FOREIGN PATENT DOCUMENTS

WO    WO 2006/017832    2/2006

OTHER PUBLICATIONS

Andrews et al., "BAM: Food Sampling/Preparation of Sample Homogenate," Bacteriological Analytical Manual, 2003, Chapter 1.
Berri, et al., "The Detection of Coxiella Burnetii from Ovine Genital Swabs, Milk and Fecal Samples by the Use of a Single Touchdown Polymerase Chain Reaction." Veterinary Microbiology, 2000, 2:285-293.
Davies et al., "Evaluation of the Use of Pooled Serum, Pooled Muscle Tissue Fluid (meat juice) and Pooled Faeces for Monitoring Pig Herds for *Salmonella*," Journal of Applied Microbiology, 2003, 95:1016-1025.
"Diarrheagenic *Escherichia coli*," U.S. Food and Drug Administration, Bacteriological Analytical Manual Online, Chapter 4A, retrieved from http://www.cfsan.fda.gov/~ebam/bam-4a.html on Jun. 17, 2008.
"Enumeration of *Escherichia coli* and the Coliform Bacteria," U.S. Food and Drug Administration, Bacteriological Analytical Manual Online, Chapter 4, retrieved from http://www.cfsan.fda.gov/~ebam/bam-4.html on Jun. 17, 2008.
Gabis, et al., "ICMSF Methods Studies, II. Comparison of Analytical Schemes for Detection of *Salmonella* in High-Moisture Foods," Canadian Journal of Microbiology, 1974, 20:663-669.
Jarvis, B., "Errors Associated with Dilution Count and Presence/Absence Methods," Statistical Aspects of the Microbiological Analysis of Foods, Progress in Industrial Microbiology, 1989. Ch. 8, vol. 21, Elsevier Science.
Jarvis, B., "Errors Associated with Quantal Response Methods," Statistical Aspects of the Microbiological Examination of Foods, 2008, Ch. 8:143-176, Academic Press, Amsterdam, London, and San Diego.
Jarvis, B., "On the Compositing of Samples for Qualitative Microbiological Testing," Letters in Applied Microbiology, 2007, 45:592-598.
Jarvis, B., "Statistical Aspects of the Microbiological Analysis of Foods. Progress in Industrial Microbiology," 1989, 21: 117-142, Elsevier Science Publishers B.V.

(Continued)

*Primary Examiner* — Jon P Weber
*Assistant Examiner* — Kailash C Srivastava
(74) *Attorney, Agent, or Firm* — Barry L. Davison; Davis Wright Tremaine LLP

(57) ABSTRACT

Provided are methods for sampling, testing and validating test lots, comprising: assembling a plurality of product portions from each of a plurality of test lots and combining the portions to provide a corresponding set of test lot samples; enriching the test lot samples; removing portions of each enriched sample, and combining the removed portions to provide a modular composite sample; and testing of the modular composite sample, and individual testing of the enriched test lot samples, using at least one suitable detection assay for a target microbe or organism, wherein when such testing is negative all test lots are validated, and wherein when such testing is positive with respect to the modular composite sample, or with respect to an individual enriched test lot sample, individual test lots may nonetheless yet be validated by further testing of a portion of respective initially-negative enriched test lot samples and obtaining negative results.

34 Claims, No Drawings

OTHER PUBLICATIONS

"Microbiological Testing Program and other Verification Activities for *Escherichia coli* O157:H7 in Raw Ground Beef Products and Raw Ground Beef Components and Beef Patty Components," US Department of Agriculture, FSIS Directive, 2004, 10.010.1, Rev. 1.

Price et al., "*Salmonella* Testing of Pooled Pre-Enrichment Broth Cultures for Screening Multiple Food Samples," Applied Microbiology, Apr. 1972, vol. 23, No. 4: 679-682.

Renter, et al., "Diversity, Frequency, and Persistence of *Escherichia coli* O157 Strains from Range Cattle Environments," Applied and Environmental Microbiology, 2003, vol. 69, No. 1:542-547.

Rohlf, F.J., et al, "Optimizing Composite Sampling Protocols," Environmental Science and Technology, 1996, vol. 30, No. 10:2899-2905.

Samadpour, et al., "Laboratory Investigation of an *E. coli* O157:H7 Outbreak Associated with Swimming in Battle Ground Lake, Vancouver, Washington," Journal of Environmental Health, 2002, vol. 64, No. 10:16-20.

Silliker et al., "ICMSF Methods Studies. I. Comparison of Analytical Schemes for Detection of *Salmonella* in Dried Foods," Canadian Journal of Microbiology, 1973, 19: 475-479.

Silliker et al., "Laboratory Methods," Food-Bourne Infections and Intoxicants, 1969, Ch. XI: 455-474, Academic Press, New York and London.

Thomas et al., "Examination of Stockfeeds for *Salmonella*," Australian Veterinary Journal, Feb. 1981, 57:69-71.

Andrews, et al., "*Salmonella*," Compendium of Methods for the Microbiological Examination of Foods, $4^{th}$ Ed., 2001, Ch. 37, American Public Health Association, pp. 357-380.

Budiman et al., "Localization of *Jointless-2* Gene in the Centromeric Region of Tomato Chromosome 12 based on High Resolution Genetic and Physical Mapping," Theoretical and Applied Genetics, vol. 108, 2004, published online Sep. 2003, pp. 190-196.

Cousin, et al., "Psychotrophic Microorganisms," Compendium of Methods for the Microbiological Examination of Foods, $4^{th}$ Ed., 2001. Ch. 13. American Public Health Association, pp. 159-166.

Entis, et al., "Rapid Methods for Detection, Identification, and Enumeration," Compendium of Methods for the Microbilogical Examination of Foods, $4^{th}$ Ed., 2001, Ch. 10. American Public Health Association, pp. 89-126.

The International Committee on Microbiological Specifications for Foods (ICMSF), "Microorganisms in Foods, 1 Their Significance and Methods of Enumeration," $2^{nd}$ Edition, 1978, University of Toronto Press, pp. 3-10 and 91-172.

Kuo, et al., "Sample Pooling to Expedite Bioanalysis and Pharmacokinetic Research," Journal of Pharmaceutical and Biomedical Analysis, vol. 16, 1998, pp. 837-846.

Meng, et al., "Pathogenic *Escherichia coli*," Compendium of Methods for the Microbiological Examination of Foods, 4th Ed., 2001, Ch. 35, American Public Health Association, pp. 331-341.

Midura, et al. "Sampling Plans, Sample Collection, Shipment and Preparation for Analysis," Compendium of Methods for the Microbiological Examination of Foods, $4^{th}$ Edition, 2001, Ch. 2, American Public Health Association, pp. 13-23.

Skov, et al., "Evaluation of Sampling Methods for the Detection of *Salmonella* in Broiler Flocks," Journal of Applied Microbiology, vol. 86, 1999, pp. 695-700.

Sperber, et al. "Cultural Methods for the Enrichment and Isolation of Microorganisms," Compendium of Methods for the Microbiological Examination of Foods, $4^{th}$ Ed., 2001, Ch. 5, American Public Health Association, pp. 45-51.

* cited by examiner

MODULAR COMPOSITING-MULTIPLE LOT SCREENING PROTOCOLS FOR DETECTION OF PATHOGENS, MICROBIAL CONTAMINANTS AND/OR CONSTITUENTS

CROSS-REFERENCE TO RELATED APPLICATIONS

The present application is a continuation of U.S. Provisional patent application Ser. No. 11/199,871, filed 8 Aug. 2005, which claims the benefit of priority to U.S. Provisional Patent Application Ser. No. 60/599,473, filed 6 Aug. 2004 and entitled MODULAR WET COMPOSITING-MULTIPLE LOT SCREENING PROTOCOLS FOR DETECTION OF PATHOGENS, both which are incorporated by reference herein in their entirety.

FIELD OF THE INVENTION

Aspects of the present invention relate generally to improving the efficiency of producing food and health related (e.g., pharmaceutical) products, and the safety and quality thereof. Particular embodiments relate to novel methods for microbial pathogen testing that allow for enhanced sensitivity, cost savings and traceability (e.g. source tracking) for remedial purposes. The methods are broadly applicable to many product areas including, but not limited to beef, pork, sheep, bison, deer, elk, poultry (e.g., chicken and turkey) and fish and other seafoods, produce, juices, dairy products, dry goods (cereals, nuts, etc), fruits and vegetables, herbs and spices, and all manners of raw and processed foods, environmental samples (water, wastewater, soil, surface samples, air samples taken by impingers and filtration, etc), pharmaceuticals, and other types of samples to be analyzed using microorganism enrichment-detection protocols.

BACKGROUND

Manufacturers and respective regulatory agencies strive to continually improve the safety and the quality of foods, pharmaceuticals, neutraceuticals, water and the environment. Under recent United States Department of Agriculture, Food Safety and Inspection Service (FSIS) directives and guidelines, many food producers in the United States have adopted sampling plans that involve testing, for example, of raw beef trims and/or ground beef for *E. coli* O157:H7, and ready-to-eat products for *Listeria monocytogenes* and/or *Salmonella*. Similar trends are observed in other countries, for products detained for domestic consumption and/or export. For example, the pharmaceutical industry spends considerable resources on sterility testing and environmental monitoring, and the water and wastewater industry and their respective regulatory agencies allocate considerable resources to monitor the quality of water (e.g., drinking, recreational and fisheries resources), wastewater (treated and untreated) and sludge (biosolids). Concern for the quality of air has resulted in monitoring of indoor air for the presence of microbial contaminants and pathogens. These sampling plans associated with such testing determine, for example, the disposition of products and the production lots, or result in decisions regarding the safety of water, receiving waters and recreational waters, and the impact of wastewater discharge, and quality of air.

The operative art with respect to such product "hold and release" monitoring efforts comprises various different sampling plans, typically pursuant to International Commission on Microbial Specifications for Food (ICMSF) guidelines for testing food products, FDA and USDA or EPA guidelines, or intuitive sampling plans. The common feature of these sampling plans is that several samples representing production lots, or a number of environmental samples, are combined into a combined production lot prior to sampling. For example, a typical plan for microbial pathogen detection calls for taking more than one sample, for instance ten (10) to sixty (60) sample pieces from a given sample lot (combined production lot), to form a composite sample for testing. The number of pieces taken to form the composite sample depends, under ICMSF or other regulatory guidelines, on the outcome of infection/poisoning (e.g., the severity), the level of hazards, and potential increase in the hazard levels due to storage. The same holds true in detecting microbial constituents and/or spoilage organisms. With respect to *E. coli* O157 testing, for example, a typical plan calls for taking 60 samples (e.g., sample pieces) from a production lot to form a single composite sample. With respect to *Listeria monocytogenes*, thirty (30) samples are typically taken from a production lot to form a composite sample. With respect to sterility testing, a typical plan may call for compositing 10-100 units of the product, and in the case of environmental sampling, 2-10 samples are often composited. Generally, the number of samples that are composited reflects: the overall sensitivity of the test method and the limit of detection that applies to the test unit; the ability to concentrate/enrich the composite sample to achieve the desired sensitivity; and the cost of sampling compared with the cost of analysis.

The costs associated with testing food are substantial, and consequently manufacturer's often resort to increasing the size of the "production lot" to be tested. For instance, the standard size production lot for trim testing for *E. coli* O157 in the U.S. beef industry is five (5) 'combos' (each combo weighing approximately 2,000 pounds), and for *Listeria* and *Salmonella* in ready-to-eat (RTE) products, it is one composite sample per production line per shift. A primary problem associated with the use of large size test lots is that a large quantity of products must be downgraded or destroyed when there is a positive finding of a pathogen. Additionally, because of the nature of combination 'lotting' (combining, for purposes of forming the test lot, several independent sub-lots that collectively span a long period of production time), it is very difficult to investigate the cause of the failure and pinpoint the source/cause, and remedial measures cannot be effectively taken. Furthermore, compositing a large number of samples may result in reduced sensitivity for the test unit and adversely effect the limit of detection.

Typically, once a composite sample is constructed (following the art with respect to particular testing) it is then enriched for the presence of a given pathogen/microbe by addition of appropriate amounts of enrichment media and incubation at an appropriate temperature for a given amount of time. If the pathogen/microbe is present, then it grows and multiplies under the favorable conditions of enrichment, thereby providing more material which can be detected by subsequent analysis. The composite sample is then tested by one or more available, art recognized methods including, for example, enrichment followed by immunoassay-based tests or PCR-based methods, or culturing of the organism of interest, or other DNA- or immunochemical-based methods.

The above-described prior art has several substantial deficiencies. First, even though the prior art production lot encompasses several production sublots (for instance 5 combo/pallets of products, or an entire shift of production), if a positive finding is obtained for the production lot (composite test sample), the entire production lot is rejected (all 5 combos/pallets, or one shift of production) and diverted to economically undesirable end uses (e.g., cooking or disposal), even though the pathogen of concern may be confined to only a limited portion of the production sublots (corresponding to one or two combos/pallets or an hour of production) comprising the production lot.

Second, the current art does not allow for retesting of any production sublots, primarily because microbial contaminants are unevenly spread throughout the products, and in many instances the levels of contamination are minute and may be present on very small portions of the products in each sublot. Therefore, once a composite sample is constructed if it tests positive all of the sublots are destroyed. The regulatory agencies do not allow for re-testing of the sublots, premised on the argument that after a production lot tests positive, negative test results obtained for production sublots, or even a new production lot composite sample, are meaningless since the microbial contaminants are not uniformly present throughout the products.

Third, the current protocols for collecting a composite sample representing a production lot often group together production sublots that are unrelated by virtue of product type or hours of production. This makes investigating the nature of the failure a difficult task even when relevant information is available. As an example, information is frequently available on a 'per combo' basis including (but not limited to) hour of production, vendor source of raw materials, production employees present, and operational status of microbial intervention process steps. However, when five unrelated combos/pallets are included in a production lot it is much harder to rationally analyze the available information since there is no way to determine which combo(s) contained the pathogen (as stated above, prior art re-sampling is not a viable option since it may not yield the same result). Likewise, for sterility testing, when the composite sample tests positive, the entire production will be disposed.

Therefore, there is a pronounced need in the art to implement novel and effective testing protocols that provide a greater measure of assurance that the food product is safe, that provide economic relief to the producer, and that allow for effective tracking of the contaminated lot(s) for remedial purposes (e.g., pinpointing the time of the contamination and determine the segment of production which was impacted).

SUMMARY OF THE INVENTION

Aspects of the present invention provide novel enrichment, testing and detection methods for detection of pathogens or other microbes in, for example, food, water, wastewater, industrial, pharmaceutical, botanical, environmental samples and other types of samples analyzed by detection methods (e.g., enrichment-detection methods). According to particular aspects, where any microbiological testing program involves compositing a number of samples to form a test lot, independent enrichment of each of the components of the composite sample is performed with subsequent formation of a modular (e.g., wet modula) composite sample by combining portions from each independent enrichment, which allows for determining the outcome of the test for each individual subunit of the composite as opposed to generalizing the results of the test sample to all of it's subunits. This individual outcome determination is achieved by retesting the individual enrichment samples in the event that the composite enrichment tests positive.

In preferred aspects, a reportable lot is defined as a single unit of a modular (e.g., modular wet) composite lot, rather than as an entire composite lot comprised of multiple sublots. For example, a reportable production lot is defined as a single unit of production and corresponds to a single unit of a modular wet composite production lot, rather than (as in the prior art) as an entire composite lot comprised of multiple production units (multiple sublots). With respect to testing each reportable lot (e.g., each single unit of production), a plurality of pieces/portions of sample are separately collected from each single reportable lot (e.g., from each single production unit; individual test unit) and composited to form, for example, one 'single-unit production lot sample' (corresponding, in each case, to a particular single unit of production), which is enriched using appropriate enrichment protocols to allow for the levels of the target organism to reach detection levels and uniformity of presence in the enriched sample. Multiple aliquots of the enrichment media may be removed for analysis, thus circumventing the prior art problem of having to re-sample a test production lot where microbial contaminants are not uniformly present throughout the product.

In the exemplary context of enriched single units of production, equal portions of enrichment buffer are removed (aseptically) from each single-unit production lot sample and combined to form a Modular Wet Composite Sample (MWCS). The MWCS is then tested using an appropriate test (detection assay) for the target agent (e.g., target organism). If a negative result is obtained from the MWCS, then all of the individual single-unit production lots are released. Significantly, if a positive result is obtained from a MWCS, the enrichment buffers from each of the individual single-unit production lot samples are separately (individually) tested, using the same test protocol, or a test protocol with enhanced sensitivity, or any appropriate test protocol. According to particular preferred aspects, the signal obtained from a MWCS is due to one or more of it's components (e.g., reportable lots (e.g., individually enriched single production units)), and it is, therefore, possible in all cases to trace a positive signal to one or more individual subunits by testing each individual enrichment sample for the same target. When a positive finding is obtained for any individual reportable lot sample (e.g., single-unit production lot sample), that particular reportable lot (e.g., single-unit production lot) is deemed to be positive, and appropriate actions are taken based on the result. In the case of pathogen/microbial testing for foods, the individual positive sublots can be diverted to cooking, disposal, or other acceptably safe endpoint. The rest of the individually enriched test units that test negative are deemed to be negative and will be reported as such (are validated).

DETAILED DESCRIPTION OF THE INVENTION

Particular aspects provide novel enrichment, testing and validation methods for detection of pathogens or other microbes in any type of samples (e.g., food production lots, water, wastewater, industrial, pharmaceutical, botanical, environmental samples, etc.) analyzable by enrichment-detection methods. In preferred aspects, a test lot (single-unit production lot), rather than (as in the prior art) a composite lot comprised of multiple test lots (e.g., single-unit production lot units), is defined and established as the single unit of production. A plurality of portions (e.g., product portions) are separately collected from each test lot (e.g., single-unit production lot) and composited to form a corresponding set of test lot samples (e.g., single-unit production lot samples), which are enriched using suitable enrichment protocols to allow target agents/organisms to reach detectable levels and sample uniformity. In particular embodiments, equal portions of enrichment buffer are removed (preferably aseptically) from the enriched samples, and combined to form a modular composite sample (e.g., modular wet composite sample; MWCS). The MWCS, for example, is tested using a suitable detection assay for the target agent/organism. If a negative result is obtained from the MWCS, then all of the individual single-unit production lots are validated and releasable. If a positive result is obtained from a MWCS, the enrichment sample corresponding to individual test lots (e.g., individual single-unit production lots) are separately (individually) tested, using the same, or a more sensitive test protocol. If a positive finding is obtained for any test lot sample (e.g., individual single-unit production lot sample), that particular respective lot is diverted to cooking, disposal, or other acceptably safe endpoint. If a negative finding is obtained for any individual test lot sample (e.g., single-unit production lot sample), then that particular lot is validated and releasable. In this manner, any member lot of the MWCS that tests negative using the same method (about 5-fold more sensitive relative to the prior art), or an enhanced method (about fifty times more sensitive), will be validated and releasable for consumption.

DEFINITIONS

The term "test lot" or "reportable lot" as used herein to refer to an assemblage of one or more specimens of a medium or process (e.g., assemblage of specimens of air, water, solids, or of products of a production process, etc.), where such assemblage can be sampled by taking portions of the one or more specimens thereof, and where the one or more specimens of the assemblage are operationally linked in a manner (e.g., proximity, time, process step, etc.) whereby information derived about sampled portions is operationally applicable to all specimens of the assemblage, and thus to the test lot. In particular instances, portions are synonymous with specimens.

The term "single production unit" or "single-unit production lot" as used herein is a form of test lot, and refers to a single unit of production (e.g. for beef trim a "combo," or for almonds a "bin") rather than, as in the prior art, to a composite comprised of multiple, non-operationally linked single production units (production sublots).

The term "product portion" as used herein refers to a product piece (e.g., a piece of solid beef trim, etc.), aliquot of product (e.g., a volume of liquid juice) or weight of product (e.g., a weight of semi-solid pudding). A single unit of production is composed of multiple product portions. In preferred embodiments, the number of product portions which comprise a single unit of production is great enough that removal of some product portions to form a sample does not impose an unacceptable economic loss to the producer. In particular instances, a product portion may be a specimen of a test lot as defined above.

The term "compositing" as used herein refers to combining a number of single product portions to form one larger sample. In preferred embodiments, the number and selection of single product portions to be combined conform to statistical-based sampling plans which seek to form a typical or average sample that is representative of the test lot (e.g., single production unit) being sampled.

The term "test lot sample" or "single-unit production lot sample" or "single production unit lot sample," as used herein refers to a sample formed by combining multiple product portions from a test lot (e.g., single production unit), such that each test sample (e.g., each single-unit production lot sample) is attributed to a particular corresponding test lot (e.g., production unit). For production lot samples, the number of portions/pieces combined many be essentially any number, but preferably is selected so as to conform to statistical-based sampling plans. Preferably the number of pieces combined is selected from the range group consisting of from about 5 to about 100, from about 10 to about 90, from about 20 to about 80, from about 30 to about 70, from about 30 to about 60, and from about 40 to about 50 product portions. Preferably, the number of independent product portions is selected so as to yield a sample size that is equal to or greater than that required by the subsequent analysis to be applied.

The term "enrichment" as used herein refers to incubating a test lot sample (e.g., single-unit production lot sample) under conditions suitable to allow levels of a target agent/organism that is present to reach detectable levels and become uniform or substantially uniform throughout the enriched test lot sample (e.g., single-unit production lot sample). Preferably, enrichment comprises addition of an amount of an enrichment medium or buffer to a sample, and incubating the sample at a favorable temperature for a period of time sufficient to allow the organism to grow and multiply.

The term "enrichment medium" as used herein refers to a mixture which contains nutrients and which has properties (e.g., pH and/or oxygen content) which favor the growth of the target agent/organism. Preferably, the enrichment medium is formulated to mimic the environment of the target agent/organism or take advantage of a known metabolic property of the target agent/organism. Preferably, the enrichment medium will omit nutrients needed by competing undesired agents/organisms. Preferably, the enrichment medium will include selective agents that will inhibit competing undesired agents/organisms. An example of an enrichment medium is that used for the isolation of nitrogen fixing bacteria (those that can use nitrogen gas as their sole nitrogen source) contains no source of fixed nitrogen in the medium. A second example is an enrichment medium for the isolation of bacteria capable of utilizing 2,4-dichlorophenoxyacetic acid (also know as 2,4-D, a common herbicide) as a source of carbon and energy. The enrichment medium is formulated to contain benzoate as the only organic compound.

The term "wet enrichment" as used herein refers to diluting a solid, semisolid or liquid single-unit production lot sample (single production unit lot sample) with enrichment medium in a ratio of approximately 1:10 (wt./v), consistent with conventional methods for expanding and testing a variety of target agents/organisms as set forth in widely recognized published methods. For example, the conventional method for expanding and testing for coliforms, fecal coliforms and $E.\ Coli$ in food, comprises a 1:10 dilution of the samples (e.g., 50 g into 450 ml) (see, e.g., U.S. FDA Bacteriology Analytical Manual Online, Chapter 4 and 4A, describing standard 1:10 dilution procedures for testing of coliforms, fecal coliforms and $E.\ Coli$ in food, shellfish and juices).

The term "dry enrichment" as used herein refers to enriching a solid, semisolid or liquid single unit production lot sample either with no addition of other compounds if the sample's intrinsic properties (water activity, nutrients and pH) are sufficient/proper to promote the growth of the target agent/organism, or by dilution of the sample with minimal amounts of enrichment medium in ratios ranging from about 0.1 (wt/v) to about 1 (wt/v).

The term "modular composite sample" as used herein refers to a sample formed by removing, preferably aseptically, equal portions of each of a plurality of enriched single-unit production lot samples, and combining the removed portions.

The phrase "suitable detection assay" as used herein refers to any assay that is suitable for detecting a particular agent/organism. Preferably, the assay is optimized to detect the particular agent/organism, and may be combined with one or more concentration steps for concentration of the agent/organism being assayed.

The term "validation" as used herein with respect to production lots refers to determining that a particular sample tests negative using the detection assay. Where a modular composite sample tests negative, all single-unit production lot samples comprising the composite sample are validated along with the respective single-unit production lots, which are thus cleared for release. Where a modular composite sample tests positive, individual single unit production lots may nonetheless yet be validated if particular respective single-unit production lot samples test negative.

"Trim" refers to small pieces of meat and fat which are excised during, for example, the beef fabrication process in order to produce primal and subprimal pieces and marketable cuts.

"Trim testing" refers to the process of testing trim, or raw materials which are to be used for ground meat production for microbial/pathogen content.

A "combo" or "combo-bin" refers, in the beef industry, to the single production unit packaging unit. Alternatively raw materials corresponding to a single production unit to be tested can be packaged into boxes, bags or other appropriate containers, which can be placed, for example, on pallets.

A "composite lot-unit" or "five-combo-lot unit" refers to a composite unit, comprised of five combos (combo-bins). In prior art sampling plans, the composite lot-unit represents the raw material (composite trim) upon which sampling, testing and acceptance or rejection is based.

Therefore, according to particular aspects, a test lot (or test unit) (e.g., a single-unit production lot or single production unit lot) is defined and taken as one or more operationally-linked specimens of a medium or process. A test lot may be a single unit of production (e.g., a single combo, bin, pallet, or segment of production, etc.), or a single environmental sample (e.g., single air sample, single water and wastewater sample, etc.), rather than, as in the prior art, as a composite of multiple production units or environmental samples.

In preferred embodiments, a number of pieces or portions of sample are collected from a test lot (e.g., from a single production unit (e.g., from the single combo, bin, pallet, or segment of production, etc.), and composited to form one 'single-unit test sample' (or 'single-unit production lot sample.' In particular embodiments (e.g., wet enrichment), enrichment buffer is added to the sample. In alternate embodiments, 'dry enrichment' (as defined herein above) is done.

Significantly, in the inventive modular (e.g., wet modular) compositing method, samples taken from each unit of production are enriched separately using appropriate enrichment protocols to allow for the levels of the target organism to reach detection levels and uniformity of presence in the enriched sample. In preferred aspects, such enrichment obviates the prior art problem of having microbial contaminants that are not uniformly present throughout the product sample. Specifically, while microbes are not necessarily uniformly distributed in food, water, air, pharmaceuticals, etc, after enriching a sample as described herein, the target microbes are uniformly, or as least substantially uniformly, present in the enrichment medium or extract from dry or semi dried enrichments.

Following incubation for the target organism, equal portions of enrichment buffer or sample are removed (aseptically) from each of several test lot samples (e.g., from several single-unit production lot samples; preferably 5) and pulled together to form a Modular Wet Composite Sample (MWCS). The MWCS is then tested using an appropriate test (detection assay) for the target organism. If a negative result is obtained from the MWCS, then all of the individual single unit production Lots are released.

If a positive result is obtained from a MWCS, the enrichment buffers from each of the individual single unit production lot samples are then separately (individually) tested, using the same test protocol, or any other appropriate tests. Alternately, an augmented protocol that uses a concentration step for the target organism, such as immunomagnetic bead separation, affinity chromatography, etc., followed by an appropriate detection method is used to test the enriched individual test lot samples (e.g., the individual single-unit production lot samples).

In preferred aspects, the inventive methods of analysis are modified by introducing a concentration step (e.g., employing antibody-coated paramagnetic beads into the procedure (e.g., DNA-based detection, biosensor based detection, classical microbiological detections, etc)). Antibody-coated paramagnetic beads, for example, afford an approximately 10-fold increase in sensitivity. This concentration step, combined with the fact that the individual test lot samples (e.g., individual single-unit production lot samples) are not 5-fold diluted relative to the MWCS, allows for an overall 50-fold increase in sensitivity relative to prior art sampling and testing protocols. If a lateral flow device is used for detection, such immunomagnetic concentration may or may not be used, in which case the detection sensitivity is increased by about 5-fold.

Where a positive finding (test result) is obtained for any individual test lot sample (e.g., single-unit production lot sample), that particular corresponding test lot (e.g., single-unit production lot) is deemed to be positive, and appropriate decisions are then made on the positive results (e.g., in the case of food products, diversion to cooking, disposal, or other acceptably safe endpoint). For each of the rest of the test lot samples (e.g., single-unit production lot samples) belonging to the positive MWCS, where a negative finding is obtained, that particular test lot sample (e.g., that single-unit production lots sample) is deemed to be negative. In this manner, any test lot (e.g., any single-unit production lot) that is a member of the group of test lots (e.g., single-unit production lots) that comprise a corresponding MWCS, will be considered to be negative, if it tests negative using the same method (about 5-fold more sensitive relative to the prior art), or the enhanced method (about fifty times more sensitive).

In alternate preferred embodiments, a new Modular Wet Composite Sample is reconstructed from the member lots (test lots) that have tested negative, and subjected to a third layer of testing to again show (confirm) that they are negative. Specifically if one of the five individual test lots (e.g., individual single-unit production lots) has tested positive (and the other four negative), and the protocols call for testing of composites consisting of five test lots, a new single test lot sample can formed from a new test lot, and can be used along with the four negative samples to form a new MWCS.

The methods of the present invention provide substantial economic savings to the food and pharmaceutical industries, because of the precision in detecting in the context of operationally-linked portions of production (e.g., test lots; single production units; single-unit production lots) which are contaminated. The inventive methods prevent unnecessary destruction of negative lots that are condemned because of guilt by association (e.g., simply because they were grouped with a contaminated composite prior art multiple production unit lot in a prior art testing protocol). Where a positive finding is obtained, a smaller quantity of material is diverted to an economically undesirable end use. The proposed invention has substantial utility (e.g., bringing savings, accuracy and precision in pinpointing problems) in the environmental industry.

Additionally, and significantly, it is easier to trace the source of the contamination and apply remedial measures, because the single-unit test component points, for example, to single point of production or a single sampling site.

Particular Preferred Aspects:

Particular aspect provide a method of sampling, testing and validating test lots, comprising: separately collecting a plurality of portions from each of a plurality of test lots, the test lots each comprising an assemblage of one or more operationally-linked specimens, wherein the assemblage can be sampled by taking portions thereof; combining the collected portions corresponding to each of the test lots to provide a corresponding set of test lot samples, wherein each test lot sample is attributed to a particular corresponding test lot; incubating the set of test lot samples under conditions suitable to allow levels of a target agent or organism that is present in one or more of the samples to reach detectable levels and become uniform, or substantially uniform, throughout the respective one or more samples, to provide a set of enriched test lot samples; removing, aseptically, equal portions of each enriched test lot sample, and combining the removed portions to provide a modular composite sample; and testing of the modular composite sample, using a suitable detection assay, for the target agent or organism, wherein where such testing is negative all test lot samples are validated, and wherein where such testing is positive, individual test lots may nonetheless yet be validated by further testing of a portion of the respective enriched test lot sample using the same or a more sensitive protocol and obtaining a negative test result.

In particular aspects, the test lot is selected from the group consisting of an environmental lot comprising one or more operationally-linked environmental specimens, pharmaceutical lot comprising one or more operationally-linked pharmaceutical specimens, single-unit product lot comprising one or more operationally-linked product specimens, and combinations thereof. In particular aspects, the test lot is a single-unit production lot, comprised of operationally-linked product specimens. In particular aspects, product specimens are synonymous with product portions. In particular aspects, the methods further comprise incubating the modular composite sample prior to testing it. In particular aspects, incubating each test lot sample comprises adding an amount of enrichment medium to the sample, and removing enriched sample portions comprises removing a portion of the enrichment medium from each enriched sample and combining the removed portions to provide a modular composite sample. In particular aspects, testing of the modular composite sample, using a suitable detection assay comprises use of a concentration step to concentrate the microbial agent or organism.

In particular aspects, where testing of the modular composite sample is positive, and wherein the individual test lots are further tested, such further testing comprises use of the more sensitive protocol. Preferably, the more sensitive protocol comprises use of a concentration step to concentrate the microbial agent or organism, in combination with the same test protocol used to test the modular composite sample.

In particular aspects, the methods further comprise forming an additional modular composite sample from the enriched test lot samples and testing the additional modular composite sample, using the same or a different suitable assay, to confirm the testing status. In particular aspects, the methods further comprise forming an additional modular composite sample from an additional enriched test lot sample along with any enriched test lot samples that test negative, and testing the additional modular composite sample, using the same or a different suitable assay. In particular aspects, the methods further comprise, where testing of the modular composite sample is negative, forming an additional modular composite sample from the enriched test lot samples, and testing the additional modular composite sample, using a different suitable assay, to confirm the negative testing status.

In particular aspects, the test lot is selected from the lot group consisting of a single combo, single bin, single pallet, and a segment of production. Preferably, the number of test lots is from about 3 to about 10, about 5 to about 8, or about 5.

In particular aspects, the methods further comprise, where testing of the modular composite sample is positive, determining which individual test lots are positive, and application of remedial measures that are specific to one or more individual test lots that test positive. In particular aspects, separately collecting a plurality of portions from each of a plurality of test lots comprises separately collecting from each test lot a number of portions selected from the group consisting of from about 5 to about 100, from about 10 to about 90, from about 20 to about 80, from about 30 to about 70, from about 30 to about 60, and from about 40 to about 50 portions. Preferably, separately collecting a plurality of portions from each of a plurality of test lots comprises separately collecting from each test lot about 30 to about 60 portions. Alternatively, separately collecting a plurality of portions from each of a plurality of test lots comprises separately collecting from each test lot about 30 portions. Preferably, separately collecting a plurality of portions from each of a plurality of test lots comprises separately collecting from each test lot about 60 portions.

Particular aspects provide a method of sampling, testing and validating test lots, comprising: separately collecting a plurality of portions from each of a plurality of single-unit production lots, the single-unit production lots each comprising an assemblage of one or more product specimens, wherein the assemblage can be sampled by taking portions thereof; combining the collected product portions corresponding to each of the single-unit production lots to provide a corresponding set of single-unit production lot samples, wherein each single-unit production lot sample is attributed to a particular corresponding single-unit production lot; incubating the set of single-unit production lot samples under conditions suitable to allow levels of a target agent or organism that is present in one or more of the single-unit production lot samples to reach detectable levels and become uniform, or substantially uniform, throughout the respective one or more samples, to provide a set of enriched single-unit production lot samples; removing, aseptically, equal portions of each enriched single-unit production lot sample, and combining the removed portions to provide a modular composite sample; and testing of the modular composite sample, using a suitable detection assay, for the target agent or organism, wherein where such testing is negative all single-unit production lot samples are validated, and wherein where such testing is positive, individual single-unit production lots may nonetheless yet be validated by further testing of a portion of the respective enriched single-unit production lot sample using the same or a more sensitive protocol and obtaining a negative test result.

The following Examples are exemplary are not intended, and should not be construed to limit the scope of the aspects of the present conception that are claimed hereunder.

Example I

The Present Inventive Methods were Shown to Provide a Substantial Economic Advantage, while Providing for Enhanced Safety, and Implementation of Remedial Measures At present, the standard size 'production lot' for trim testing for *E. coli* O157 in the beef industry in the USA is a combination of five combos, where each combo represents a single production unit and weighs approximately 2,000 pounds. An inventive modular composite sample method, and in particular a Modular Wet Composite Sample (MWCS) method was implemented at a United States beef producer.

However, when five unrelated combos are included in a combined 'production lot' (as in the prior art) it is much harder to rationally analyze the available information since there is no way to determine which combo(s) contained the pathogen (as stated above, prior art re-sampling is not a viable option since it may not yield the same result).

By contrast, in this Example I and according to preferred aspects of the present invention, any combo-specific information including, but not limited to hour of production, vendor source of raw materials, production employees present, and operational status of microbial intervention process steps can be brought to bear in the context of the 391 individual single-unit production lots yielding a positive sample result, thereby providing an effective means not only to trace contamination, but also to affect remedial measures in view thereof.

TABLE 1

Results of modular wet composite sampling of 62,919 multiple lots and number of Individual Production Unit Lot (IPUL) which tested positive when MWCS tested positive

| Location | Total # Analyses | # Positives | 1 IPUL | 2 IPULs | 3 IPULs | 4 IPULs | 5 IPULs |
|---|---|---|---|---|---|---|---|
| Est. A, B, C. | 62,919 | 271 | 180 | 39 | 18 | 11 | 7 |

TABLE 1 shows, according particular aspects, the result of testing 62,919 MWCS samples, and then retesting the individual single-unit production lot (combo) samples whenever a positive result was obtained from the MWCS sample.

TABLE 1 shows that out of 62,919 MWCS samples, a total of 217 yielded a positive testing result for *E. coli* O157. Using prior art protocols, all of the single-unit production lots that comprised the 271 positive samples would go to rendering or be downgraded for cooking. As each MWCS represents five single-unit production lots of 2,000 lbs each, this would represent approximately 2,710,000 pounds of product (i.e., 271×5×2,000 pounds=2,710,000 pounds).

Specifically, the individual single-unit production lot samples comprising the MWCS were analyzed separately following each positive MWCS result. As can be seen in TABLE I, only 391 individual single-unit production lot samples yielded a positive result out of the cumulative total of 1,085 individual single-unit production lot samples comprising the MWCS samples which yielded a positive result. If only the 391 individual single-unit production lots yielding a positive sample result were diverted to rendering or downgraded for cooking this would represent 782,000 lbs of product. The remaining 694 individual single-unit production lots, corresponding to 1,928,000 lbs of product, are, according to preferred aspects of the present invention, validated and releasable into the chain of commerce.

The product, in this Example I, being produced by this U.S. beef producer was beef trim. The release of the validated 19,280,000 lbs of beef trim into commerce using the present invention, instead of diverting or downgrading the product, trim, represents a cost savings to the producer of about $2,500,000, relative to prior art methods. Additionally, the testing of the single-unit production lots by augmented testing protocols (representing a 5- to 50-fold increase in sensitivity relative to the MWCS testing) provides substantial additional assurance of the safety of the food products.

Furthermore, as outlined above under "BACKGROUND," information is frequently available on a 'per combo' basis including, but not limited to hour of production, vendor source of raw materials, production employees present, and operational status of microbial intervention process steps.

Example II

According to Particular Aspects of the Present Invention, the Inventive Sampling Methods have Substantial Utility in the Context of Ready-to-Eat (RTE) Products (E.g., Meat and Poultry Products)

Under United States Department of Agriculture, Food Safety and Inspection Service (USDA FSIS) guidelines, producers of Ready-to-Eat (RTE) meat and poultry products may adapt an 'end product' sampling program as verification that their product is free of the pathogen *Listeria monocytogenes*. The frequency of end product sampling is selected by the producer/establishment, based on valid sampling statistics. Typically, samples are collected at random times over a production shift (e.g., from 'cleanup to cleanup'), and from several product lines. The samples are combined to form a composite sample, and enrichment buffer is added to the composite sample to allow *Listeria* spp. or *L. monocytogenes* to grow and multiply under the favorable conditions of enrichment, thereby providing more material that can be detected by subsequent analysis.

According to particular aspects of the present invention the producer of RTE meat or poultry products collects samples from individual single-unit production lots. Preferably, the producer defines and produces these single-unit lots in such a fashion as to maximize the information available for investigating the nature of a failure. For example, possible definitions of an individual single-unit production lot include, but are limited to all of the product produced by a particular production line (or produced by a particular production line in a particular period of time), a volume of product such as a pallet of packed boxes produced on a particular production line, or a production area in the plant, etc.

Individual single-unit production lot samples are collected, to which, in wet enrichment embodiments, enrichment medium/buffer is added. Following incubation under conditions suitable to allow levels of a target agent or organism that is present to reach detectable levels and become uniform or substantially uniform throughout the respective sample(s), aliquots of the enrichment medium/buffers from individual single-unit production lot samples are combined to form a MWCS. The MWCS is then analyzed for the presence or absence of, for example, *Listeria* spp. or *L. monocytogenes*. In the event that a positive result is obtained for the MWCS, enrichment medium/buffer sample from the individual single-unit production lot samples comprising that MWCS is analyzed using the same, or augmented testing protocols.

Individual single-unit production lots for which the enrichment medium/buffer from the corresponding sample yields a positive result are diverted to cooking, disposal or other safety endpoint. Individual single-unit production lots for which the enrichment medium/buffer from the corresponding sample yields a negative result are released into commerce. The latter fraction represents a direct cost savings to the producer relative to a prior art approaches where a 'production lot' is defined to include multiple single-unit production lots (e.g., multiple product lines and an extended period of time ('cleanup to cleanup')).

Furthermore, by defining and establishing the individual single-unit production lots in such a fashion as to maximize the information available for investigating the nature of a failure, the producer is able to narrow the scope of investigation and apply remediative resources more effectively and efficiently. For example, where a positive result(s) is associated with one or more specific production lines, targeted aggressive sanitation is used to resolve the problem. Alternatively, for example, where a positive result(s) is associated with one or more specific products, determining whether raw materials are contaminated, or whether process microbial intervention steps were operating properly are effectively and efficiently used.

Example III

According to Particular Aspects of the Present Invention, the Inventive Sampling Methods have Substantial Utility for Providing Cost-Effective and Effective Monitoring Means for Pathogen Levels in Nut Products (e.g., Almond Products) and the Like A large number of almond products may be produced by using one or more processes including slivering, scalding, blanching, slicing, roasting, and dicing. Anti-microbial treatments may also be applied, such as use of propylene oxide. In practice, these processes may be used in many various combinations, and the output from one process may be the input for another. This makes it very difficult to trace finished product all the way back to raw materials.

As indicated by a recent outbreak, almond products are susceptible to contamination by *Salmonella* spp. According to additional aspects, the present inventive methods provide a cost-effective means of implementing an effective monitoring program for pathogen levels in nut products (e.g., almond products). In such embodiments, final almond products of each type are collected at random times over a production shift. The producer defines and establishes individual single-unit production lots as the amount of product produced during a production shift (from 'cleanup to cleanup'), or as some smaller production unit (e.g., a 'truckload'), provided that one sample was collected from each such single-unit production lot. The single-unit production lot samples are combined to form a corresponding composite sample, and, in wet enrichment embodiments, enrichment medium/buffer is added to the composite sample to allow *Salmonella* spp. to grow and multiply under the favorable conditions of enrichment (as described herein above), thereby providing more material that can be detected by subsequent analysis.

Aliquots of the enrichment medium/buffers from individual single-unit production lot samples are combined to form a MWCS. The MWCS are analyzed for the presence or absence, for example, of *Salmonella* spp. Where a positive result is obtained for the MWCS, each enrichment buffer from the individual single-unit production lot samples comprising that MWCS is analyzed using the same, or augmented testing protocols.

Individual single-unit production lots for which the enrichment buffer from the corresponding sample yields a positive result are returned for application of additional microbial intervention steps (e.g., roasting), or are diverted to a safe endpoint (e.g., a cooked product). Individual single-unit production lots for which the enrichment buffer from the corresponding sample yields a negative result are thereby validated and are releasable into commerce. The latter fraction represents a direct cost savings to the producer relative to prior art approaches where effective testing is not done, and discovery of contamination with a pathogen leads to large scale recalls of product.

Furthermore, by defining and establishing the individual production single-unit production lots in such a fashion as to maximize the information available for investigating the nature of a failure, the producer is able to narrow the scope of investigation and apply remediative resources more effectively and efficiently. For example, the processes used to produce the almond product(s) yielding positive result(s) are rationally analyzed, and associations between the pathogen contamination and one or more of the processes of slivering, scalding, blanching, slicing, roasting, and dicing are determined, and targeted effective and efficient remedial measures are applied.

Example IV

According to Particular Aspects of the Present Invention, the Inventive Sampling Methods have Substantial Utility in the Context of Contaminants that Enter a Production Line at a Given Time Point, and then Clear Sterility testing of food and pharmaceuticals, or purity testing of fermentation processes often involves compositing a number of samples to form a composite test lot. Detection of microbial contamination in the composite sample, as discussed in detail herein above, results in rejection of the whole production. Practically speaking, often a pinpoint contaminant enters production at a given time point, and then clears within a few minutes. Aspects of the present invention allow for identifying the time of entry, and informed elimination of products (operationally linked test lots) flanking the contamination event.

Example V

According to Particular Aspects of the Present Invention, the Inventive Sampling Methods have Substantial Utility in the Context of Environmental Monitoring (E.g., with Samples of Water, Wastewater, Sludge, Soil, Surface Sponges, Surface Swabs, Condensates, Air or Liquids)

In the context of environmental monitoring, when several samples (water, wastewater, sludge, soil, surface sponges, surface swabs, condensates, air or liquids) are composited and subjected to enrichment, followed by testing to detect environmental contamination, the current invention allows for pinpointing the test lots (e.g., operationally-linked unit(s)) that are positive for the microbe of concern.

The invention claimed is:
1. A method of sampling, testing and validating test lots for microbial contamination, comprising:
  a) collecting a plurality of portions from each of a plurality of test lots, the test lots each comprising an assemblage of one or more specimens, wherein each test lot is separately sampled by taking said plurality of portions thereof;
  b) combining the collected plurality of portions corresponding to each of the separate test lots to provide a corresponding set of separate test lot samples, wherein each separate test lot sample is attributed to a particular corresponding separate test lot;
  c) incubating the set of separate test lot samples under conditions suitable to allow levels of a target microbial agent or organism that is present in one or more of the separate test lot samples to reach detectable levels and become uniform, or substantially uniform, throughout the respective one or more separate test lot samples, to provide a set of separate test lot samples enriched for the target microbial agent or organism;
  d) removing portions of each enriched separate test lot sample, and combining the removed portions to provide a modular composite sample; and
  e) testing of the modular composite sample, and individual testing of each of the enriched separate test lot samples, using at least one suitable detection assay, for the target microbial agent or organism, wherein when such testing is negative all of said separate test lot samples are validated, and wherein when such testing is positive with respect to the modular composite sample, or with respect to an individual enriched separate test lot sample, individual separate test lots may nonetheless yet be validated by further testing of a portion of respective initially negative enriched separate test lot samples using the same or a more sensitive protocol and obtaining a negative test result.

2. The method of claim 1, wherein the test lot is selected from the group consisting of an environmental lot comprising one or more operationally-linked environmental specimens, pharmaceutical lot comprising one or more operationally-linked pharmaceutical specimens, single-unit product lot comprising one or more operationally-linked product specimens, and combinations thereof.

3. The method of claim 1, wherein the test lot is a single-unit production lot, comprised of operationally-linked product specimens.

4. The method of claim 3, wherein product specimens are synonymous with product portions.

5. The method of claim 1, further comprising incubating the modular composite sample of d), prior to testing in e).

6. The method of claim 1, wherein incubating each separate test lot sample in c) comprises incubating each separate test lot sample with enrichment medium suitable to enrich for the target microbial agent or organism, and wherein removing in d) comprises removing a portion of the enrichment medium from each enriched separate test lot sample and combining the removed portions to provide a modular composite sample.

7. The method of claim 1, wherein testing of the modular composite sample and enriched test lot samples, using at least one suitable detection assay further comprises a concentration step to concentrate the microbial agent or organism.

8. The method of claim 1, wherein testing in e) of the modular composite sample is positive, and wherein the individual separate test lot samples are further tested, such further testing comprises the more sensitive protocol.

9. The method of claim 1, further comprising, forming an additional modular composite sample from the set of enriched separate test lot samples of c) and testing the additional modular composite sample, using the same or a different suitable assay, to confirm the testing results.

10. The method of claim 1, further comprising, forming an additional modular composite sample from an additional enriched separate test lot sample along with any enriched separate test lot samples of c) that test negative in e), and testing the additional modular composite sample, using the same or a different suitable assay.

11. The method of claim 1, further comprising, where testing of the modular composite sample in e) is negative, forming an additional modular composite sample from the set of enriched separate test lot samples of c), and testing the additional modular composite sample, using a different suitable assay, to confirm the negative testing status.

12. The method of claim 1, wherein the test lot is selected from the lot group consisting of a single combo, single bin, single pallet, and a production assemblage.

13. The method of claim 1, wherein the number of separate test lots is from 3 to 10.

14. The method of claim 1, further comprising, where testing of the modular composite sample is positive, determining which individual separate test lots are positive, application of remedial measures to said separate positive test lots, and validating by further testing of a portion of the respective remediated separate test lots and obtaining a negative test result.

15. The method of claim 1, wherein, in a), separately collecting a plurality of portions from each of a plurality of test lots comprises separately collecting from each test lot a number of portions from 5 to 100.

16. The method of claim 1, wherein, in a) separately collecting said plurality of portions from each of said plurality of separate test lots comprises separately collecting from each separate test lot 30 to 60 portions.

17. The method of claim 1, wherein, in a) separately collecting said plurality of portions from each of said plurality of separate test lots comprises separately collecting 30 portions from each separate test lot.

18. The method of claim 1, wherein, in a) separately collecting said plurality of portions from each of said plurality of separate test lots comprises separately collecting from each separate test lot about 60 portions.

19. A method of sampling, testing and validating test lots for microbial contamination, comprising:
  a) collecting a plurality of portions from each of a plurality of single-unit production lots, the single-unit production lots each comprising an assemblage of one or more product specimens, wherein each single-unit production lot is separately sampled by taking said plurality of portions thereof;
  b) combining the collected plurality of product portions corresponding to each of the separate single-unit production lots to provide a corresponding set of separate single-unit production lot samples, wherein each separate single-unit production lot sample is attributed to a particular corresponding separate single-unit production lot;
  c) incubating the set of separate single-unit production lot samples under conditions suitable to allow levels of a target microbial agent or organism that is present in one or more of the separate single-unit production lot samples to reach detectable levels and become uniform, or substantially uniform, throughout the respective one or more separate single-unit production lot samples, to provide a set of separate single-unit production lot samples enriched for the target microbial agent or organism;

d) removing portions of each enriched separate single-unit production lot sample, and combining the removed portions to provide a modular composite sample; and e) testing of the modular composite sample, and individual testing of each of the enriched separate test lot samples, using at least one suitable detection assay, for the target microbial agent or organism, wherein when such testing is negative all of said separate single-unit production lot samples are validated, and wherein when such testing is positive with respect to the modular composite sample, or with respect to an individual separate enriched test lot sample, individual separate single-unit production lots may nonetheless yet be validated by further testing of a portion of respective initially negative enriched separate single-unit production lot samples using the same or a more sensitive protocol and obtaining a negative test result.

20. The method of claim 1, wherein removing portions in step d) is removing equal portions, aseptically, so as to preclude contamination of the enriched separate test lot samples.

21. The method of claim 1, wherein the target microbial agent or organism comprises at least one selected from the group consisting of *Listeria, Salmonella* and *Escherichia coli*.

22. The method of claim 1, wherein the target microbial agent or organism comprises at least one selected from the group consisting of *Listeria* spp., *Listeria monocytogenes*, *Salmonella* spp., *Escherichia coli* O157:H7, coliforms and fecal coliforms.

23. The method of claim 1, wherein the target microbial agent or organism comprises a spoilage organism.

24. The method of claim 1, wherein removing portions of each enriched separate test lot sample comprises removing equal volume portions of each enriched separate test lot sample.

25. The method of claim 1, wherein testing of the modular composite sample, using a suitable detection assay comprises use of at least one of a DNA-based method, an immunochemistry-based method, and a biosensor-based method.

26. The method of claim 1, wherein the separate test lots are production lots of a meat or poultry product, comprising an assemblage of one or more meat or poultry specimens, respectively.

27. The method of claim 1, wherein the separate test lots are production lots of a fish or seafood product, comprising an assemblage of one or more fish or seafood specimens, respectively.

28. The method of claim 1, wherein the separate test lots are production lots of a ready-to-eat product.

29. The method of claim 6, wherein the medium comprises a selective agent that will inhibit a competing non-target microbial agent or organism.

30. The method of claim 7 wherein the concentration step comprises at least one of immunomagnetic bead separation, and affinity chromatography.

31. The method of claim 8, wherein the more sensitive protocol further comprises a concentration step to concentrate the microbial agent or organism, in combination with the same test protocol used to test the modular composite sample.

32. The method of claim 19, wherein removing portions in step d) is removing equal portions, aseptically, so as to preclude contamination of the enriched separate single-unit production lot samples.

33. The method of claim 26, wherein the meat or poultry specimens are meat trim pieces or poultry trim pieces, respectively.

34. The method of claim 26, wherein the meat is that of beef, pork, sheep or bison.

* * * * *